(12) United States Patent
Lafont et al.

(10) Patent No.: US 7,743,481 B2
(45) Date of Patent: Jun. 29, 2010

(54) STENT CRIMPING

(75) Inventors: Antoine Lafont, Paris (FR); Serge Piranda, Besancon (FR); Patrick Sabaria, Saint Nom la Breteche (FR); Tahmer Sharkawi, Saint Jean de Vedas (FR); Michel Vert, Castelnau-le-Lez (FR)

(73) Assignee: Arterial Remodelling Technologies, Inc., Noisy-le-Roi (FR)

( * ) Notice: Subject to any disclaimer, the term of this patent is extended or adjusted under 35 U.S.C. 154(b) by 882 days.

(21) Appl. No.: 10/541,421

(22) PCT Filed: Jun. 2, 2005

(86) PCT No.: PCT/EP2005/006511

§ 371 (c)(1),
(2), (4) Date: Jan. 26, 2006

(87) PCT Pub. No.: WO2006/117016

PCT Pub. Date: Nov. 9, 2006

(65) Prior Publication Data

US 2008/0028594 A1    Feb. 7, 2008

(30) Foreign Application Priority Data

Apr. 29, 2005   (EP) .................................. 05290942

(51) Int. Cl.
*B21D 39/00* (2006.01)
*B23P 19/04* (2006.01)
(52) U.S. Cl. .......................................... 29/516; 29/235
(58) Field of Classification Search ................... 29/516, 29/508, 506, 469, 428, 235, 234, 282, 283, 29/275; 606/198, 108, 190.2
See application file for complete search history.

(56) References Cited

U.S. PATENT DOCUMENTS

| 5,810,873 A | 9/1998 | Morales |
| 5,893,867 A * | 4/1999 | Bagaoisan et al. .......... 606/198 |
| 5,911,452 A | 6/1999 | Yan |

(Continued)

FOREIGN PATENT DOCUMENTS

EP    630 623 A2    12/1994

(Continued)

OTHER PUBLICATIONS

International Search Report from PCT/EP2005/006511 (prior number assigned by French Patent Office PCT/FR2005/01354).

*Primary Examiner*—John C Hong
(74) *Attorney, Agent, or Firm*—Calfee, Halter & Griswold LLP

(57) ABSTRACT

Methods of crimping polymeric stents that simultaneously apply a radial force to the stent to reduce the diameter of the stent and a longitudinal force to elongate of the stent. According to one such method, a stent is inserted into an elastic tube having an inner surface that defines a passage. The tube is pulled to cause stretching of the tube. When the tube is stretched, the inner surface of the tube engages an outer surface of the stent and applies simultaneous longitudinal and radial forces to the outer surface of the stent. The simultaneously applied longitudinal and radial forces simultaneously reduce a radial extent of the stent and increase a longitudinal extent of the stent.

19 Claims, 5 Drawing Sheets

U.S. PATENT DOCUMENTS

| | | |
|---|---|---|
| 5,920,975 A | 7/1999 | Morales |
| 5,928,258 A | 7/1999 | Khan et al. |
| 5,969,970 A | 10/1999 | Rhoades |
| 6,009,614 A | 1/2000 | Morales |
| 6,063,102 A | 5/2000 | Morales |
| 6,096,027 A | 8/2000 | Layne |
| 6,224,627 B1 | 5/2001 | Armstrong et al. |
| 6,309,383 B1 | 10/2001 | Campbell et al. |
| 6,352,547 B1 | 3/2002 | Brown et al. |
| 6,640,412 B2 | 11/2003 | Iancea |
| 6,651,478 B1 | 11/2003 | Kokish |
| 6,702,845 B1 | 3/2004 | Cully et al. |
| 6,745,445 B2 | 6/2004 | Spilka |
| 6,783,542 B2 | 8/2004 | Eidenschink |

FOREIGN PATENT DOCUMENTS

| | | |
|---|---|---|
| EP | 903 122 A2 | 3/1999 |
| EP | 1295570 | 3/2003 |
| WO | WO 99/48439 | 9/1999 |
| WO | WO 99/56668 | 11/1999 |
| WO | WO 01/21110 | 3/2001 |
| WO | WO 03/034940 | 5/2003 |
| WO | WO 2004/075460 A2 | 9/2004 |

* cited by examiner

STENT CRIMPING

FIELD OF THE INVENTION

The present disclosure relates generally to stent crimping methods, and more particularly, the present disclosure relates to polymeric stent crimping methods that simultaneously apply longitudinal and radial forces to polymeric stents.

BACKGROUND OF THE INVENTION

A common method of treatment used in restoring blood flow through a diseased segment of a blood vessel is balloon angioplasty. The therapy generally involves the use of a balloon catheter. The balloon catheter is introduced into the cardiovascular system of a patient through the brachial or femoral artery and advanced through the vasculature until the balloon attached to the distal end of the catheter reaches the diseased vessel. The balloon is placed across the diseased vessel segment and is inflated. The balloon is then deflated to a small profile, so that the balloon catheter may be withdrawn from the patient's vasculature and the blood flow resumed through the dilated artery.

Angioplasty of an artery to correct flow obstruction in the vessel may stimulate excess tissue proliferation which then blocks (restenosis) the newly reopened vessel. The physician may need to perform a second angioplasty procedure or perform a more drastic procedure, such as a surgical bypass operation. To reduce the likelihood of restenosis and to strengthen the diseased vessel segment, an intravascular stent may be implanted within the segment of the diseased vessel. The stent is typically transported through the patient's vasculature while the stent has a small delivery diameter. The stent is then expanded to a larger diameter, often by the balloon portion of the catheter.

Stents are tubular structures, which are radially expandable to hold a narrowed blood vessel in an open configuration. Stents are most often used to support blood vessels. Stents can also be used to reinforce collapsed or narrowed tubular structures in the respiratory system, the reproductive system, biliary ducts or any other tubular body structure.

Since a catheter and a stent travel through the patient's vasculature, the stent has a small delivery diameter. The stent is positioned on a balloon catheter, such that the stent does not interfere with the vasculature during delivery, and the stent does not slip off the catheter before the stent reaches the desired location for deployment.

A stent is typically crimped onto a balloon portion of a catheter to reduce the diameter of the stent and to prevent the stent from sliding off the catheter when the catheter is advanced through a patient's vasculature. Non-uniform crimping can damage the stent and/or may result in a compressed stent/catheter profile that is larger than intended. If a stent is not securely crimped onto the catheter, the stent may slide off the catheter and into the patient's vasculature prematurely. It is important to ensure the proper compression of a stent onto a catheter in a uniform and reliable manner.

Many devices have been proposed for crimping stents onto catheters. Crimping of metallic stents is usually performed by a plier-type crimping device that cause diameter reduction. With metal stents, use of a plier-type crimping device does not inhibit simultaneous elongation of the metal stent because of the relatively high mechanical strength and the low friction coefficient of the metal stent.

SUMMARY

The present application relates to methods of crimping polymeric stents. In this application, crimping refers broadly to reducing the radial extent of a stent. According to an exemplary crimping method, a polymeric stent is inserted into an elastic tube having an inner surface that defines a passage. The tube is pulled to cause stretching of the tube. When the tube is stretched, the inner surface of the tube engages an outer surface of the stent and applies simultaneous longitudinal stretching and radial contracting forces to the outer surface of the stent. The simultaneously applied longitudinal and radial forces simultaneously reduce a radial extent of the stent and increase a longitudinal extent of the stent.

The tube can be pulled in a variety of different ways. For example, first and second end portions of the tube may be pulled in opposite directions or the position of one end of the tube may be secured, while the second end of the tube is pulled.

After the stent is compressed by the elastic tube, the tube may be released to allow the tube to return to a substantially undeformed size. After the tube is released, the crimped stent may be removed from the tube.

The tube may be made from a variety of different materials. For example, the tube can be made from an elastomer, such as silicone and silicone derivatives, or other elastomers, such as natural rubber (polyisoprene), synthetic rubber (polyisobutylene), polyurethane or any elastomers allowing large elastic radial and longitudinal deformation. For example, elastomeric tubes that can extend by factors of 150% to 2000% and reduce diameter up to the desired stent diameter can be used.

In one embodiment, a predetermined size and shape is imparted to the stent before the stent is crimped. This size and/or shape may correspond to the intended size and/or shape of the stent when deployed in the patient's vasculature.

In one embodiment, the polymeric stent is heated before the stent is crimped by the tube. For example, the stent may be heated to a temperature around the glass transition temperature of the stent before crimping the stent. In an exemplary embodiment, the polymeric stent is heated at or close to the glass transition temperature Tg for such a short enough time that the size and shape imparted previously to the stent is retained by the stent. After the stent is compressed, the stent may be cooled. In one embodiment, the cooled stent is removed from the tube.

In one embodiment, a diameter setting member is used to set the diameter of the stent to be crimped. The diameter setting member may be a cylindrical member, such as a steel. In one embodiment, a diameter setting member is used to set an intermediate smaller diameter of the stent to be crimped. The diameter setting member is removed from the partially contracted stent so that an angioplasty balloon can be inserted within the stent. Crimping of the stent is then completed using a crimping device or an elastic tube again.

Stents are often crimped onto angioplasty balloons. Stents crimped according to the disclosed methods may be crimped to angioplasty balloons in a variety of different ways. For example, a stent may be crimped directly onto an angioplasty balloon by pulling the tube, or the size of the stent may be reduced by pulling the tube and the stent is crimped to the angioplasty balloon using a second crimping device.

In one embodiment, a solvent is added to the tube to expand the tube before the polymeric stent is placed in the tube. The solvent is evaporated to bring the tube into contact with the stent. The tube is then pulled and stretched to crimp the stent.

An example of one apparatus for crimping polymeric stents includes an elastic tube and an actuator. The elastic tube has an inner surface that defines a passage that is sized to fit over the outer surface of the stent. The actuator is coupled to the elastic tube. Movement of the actuator increases a length of the elastic tube and decreases an extent of the passage. The inner surface of the tube engages the outer surface of the stent and reduces radial extent of the stent, while allowing an increase in length of the stent. The deformation of the stent follows the deformation of the tube.

Further advantages and benefits will become apparent to those skilled in the art after considering the following description and appended claims in conjunction with the accompanying drawings.

DETAILED DESCRIPTION

The present disclosure is directed to methods of crimping polymeric stents 10. In this application, crimping refers broadly to reducing the radial extent of a stent. Applicant has found that the use of existing crimping devices, such as plier-type crimping devices, inhibits elongation of polymeric stents during the crimping process. Elongation of polymeric stents is inhibited by the plier-type devices, because the plier-type devices frictionally engage the polymeric stent to inhibit elongation of the stent and typically only apply a radial compressive force to the stent. The use of existing crimping devices with polymeric stents in a glassy rigid state can break or crack the polymeric stent.

The present exemplary methods of crimping stents simultaneously apply a radial force to the stent 10 to reduce the diameter of the stent and a longitudinal force to the stent 10 to elongate the stent. The application of both radial and longitudinal forces to a polymeric stent 10 causes the stent to elongate. The simultaneous application of both longitudinal force and radial force avoids or at least minimizes the stress caused by friction opposing elongation that is generally present when existing crimping devices that do not account for elongation are used to crimp polymeric stents. By using a crimping device that exerts simultaneous contraction and elongation forces, the polymeric stent is able to elongate and contract simultaneously to minimize or eliminate traumatic force that results from friction that opposes elongation. The elongation of the stent facilitates a homogeneous reduction in the diameter of a polymeric stent.

Figure 1:
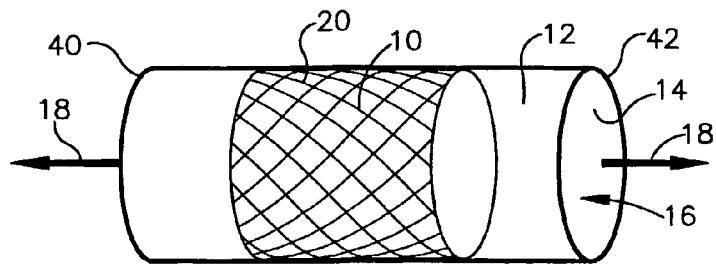
FIG. 1 is a schematic illustration of an elastic tube with a polymeric stent disposed inside the elastic tube.
Figure 2:
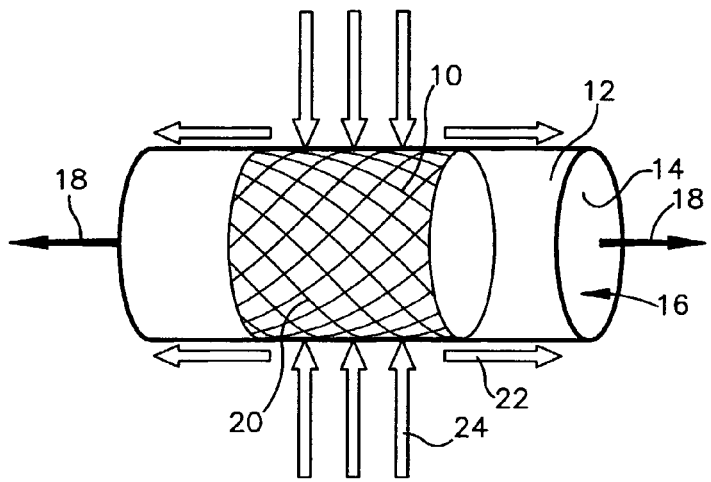
FIG. 2 is a schematic illustration of the stresses applied by the elastic tube onto the stent disposed inside the elastic tube when the tube is stretched.
Figure 3:
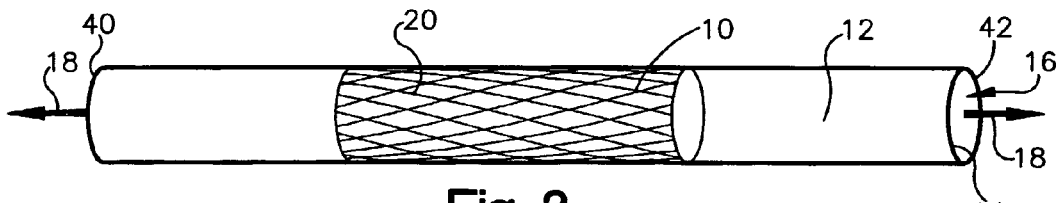
FIG. 3 is a schematic illustration of a crimped stent inside the stretched elastic tube.
Figure 4:
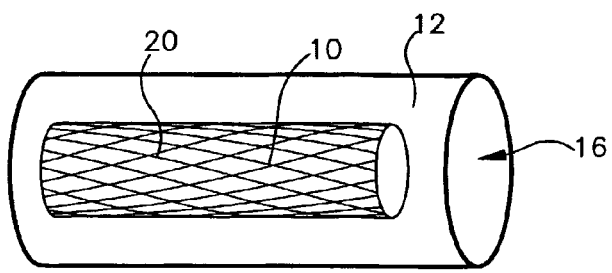
FIG. 4 is a schematic illustration of a crimped stent disposed in an elastic tube after relaxation of the tube.

FIGS. 1-15 schematically illustrate exemplary methods of crimping polymeric stents 10 by pulling and stretching an elastic tube 12. FIGS. 1-4 illustrate one method of crimping stents by pulling and stretching an elastic tube 12. Referring to FIG. 1, a stent 10 is inserted into an elastic tube 12 having an inner surface 14 that defines a passage 16. The tube is pulled as indicated by arrows 18 to cause stretching of the tube. Referring to FIG. 2, when the tube is stretched, the inner surface 14 of the tube engages an outer surface 20 of the stent 10. The inner surface 14 simultaneously applies longitudinal forces (indicated by arrows 22) and radial forces (indicated by arrows 24) to the outer surface 20 of the stent. Referring to FIG. 3, the simultaneously applied longitudinal and radial forces simultaneously reduce a radial extent of the stent and increase a longitudinal extent of the stent. Referring to FIG. 4, after the stent 10 is compressed by the tube 12, the tube may be released to allow the tube to return to a substantially undeformed size. After the tube is released, the crimped stent 10 may be removed from the tube.

The tube may be made from a variety of different materials. For example, the tube can be made from an elastomer, such as silicone rubber or silicone copolymers, or other elastomers, such as natural rubber (polyisoprene), synthetic rubber (polyisobutylene), polyurethane rubber, etc. The tube could be made from any elastomeric organic material. Materials that are highly elastic and exhibit a reduction in diameter when stretched by factors of 150% to 2000% can be used. A highly elastic tube will adhere to the stent to ensure a simultaneous application of the radial and longitudinal forces to the stent. In the exemplary embodiment, the stent 10 is made from a thermoplastic polymer that is heated to a rubbery state for crimping. In an embodiment where a desired final size and shape of the stent is previously imparted to the stent, the temperature and time of the heating to the rubbery state is selected such that the previously imparted size and shape are not erased.

In the exemplary embodiment illustrated by FIGS. 1-4, the tube has a diameter that is slightly larger than the diameter of the stent, such that the polymeric stent is snugly fit inside the tube. The elastic tube elongates from being pulled upon. This elongation also causes a radial reduction of the tube diameter. Since the stent is snugly situated inside the tube, the stent is deformed in the same manner as the tube. The snug fit between the tube and the stent insures an adherence between the outer surface of the stent and the inner surface of the tube. This adherence causes an application of the longitudinal force to the stent at the same time as the radial compression caused by the reduction in diameter of the tube that occurs when the tube is stretched.

Figure 5:
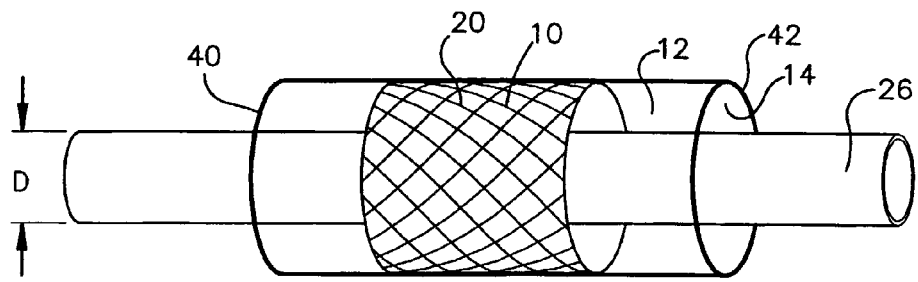
FIG. 5 is a schematic illustration of an elastic tube with a stent disposed inside the elastic tube and a diameter setting member disposed inside the stent.
Figure 6:
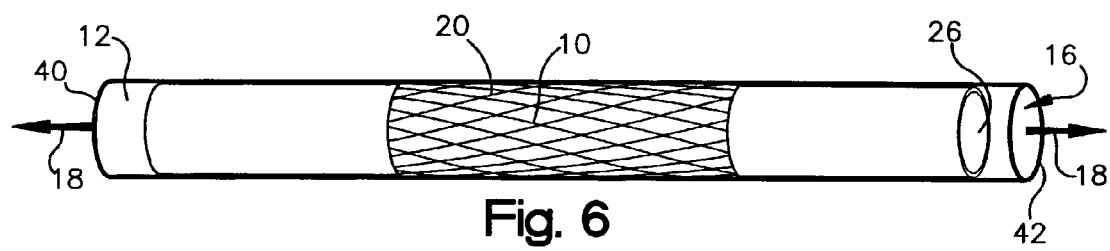
FIG. 6 is a schematic illustration of a stent being crimped by an elastic tube around a diameter setting member.
Figure 7:
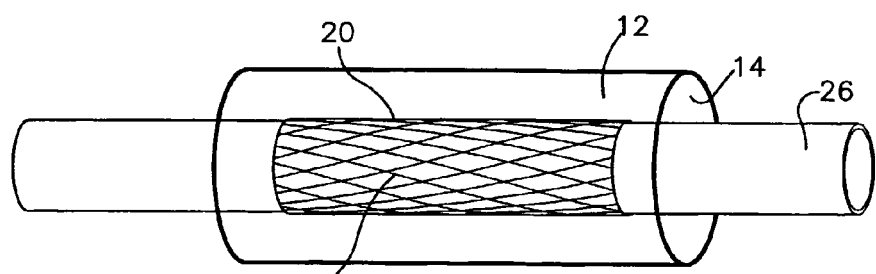
FIG. 7 is a schematic illustration of a crimped stent and a diameter setting member disposed in an elastic tube.

FIGS. 5-7 illustrate an embodiment where a diameter setting member 26 is used to set the diameter D of the crimped polymeric stent 10. In the example illustrated by FIGS. 5-7, the diameter setting member 26 is a cylindrical member, such as a steel rod. The diameter setting member 26 could also be an inflatable device, such as an angioplasty balloon. Referring to FIG. 5, the diameter setting member 26 is inserted into the stent that is disposed in the elastic tube 12. Referring to FIG. 6, the stent 10 is crimped by pulling and stretching the elastic tube. Referring to FIG. 7, the diameter setting member 26 defines the diameter of the crimped stent. In the example illustrated by FIGS. 5-7, after the elastic tube 12 is allowed to return to its original size, the stent 10 may be slid off the diameter setting member 26.

Figure 8:
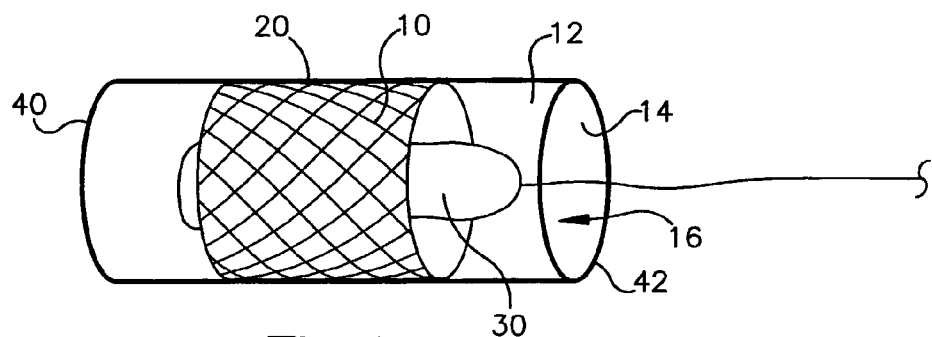
FIG. 8 is a schematic illustration of an elastic tube with a stent disposed inside the elastic tube and an angioplasty balloon disposed inside the stent.
Figure 9:
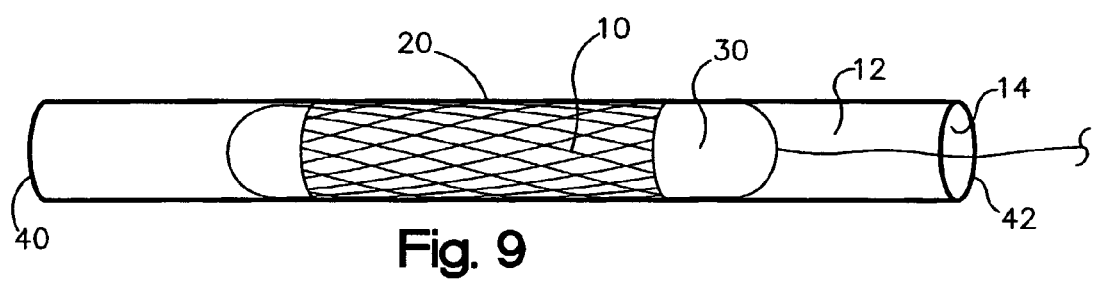
FIG. 9 is a schematic illustration of a stent being crimped by an elastic tube around an angioplasty balloon.
Figure 10:
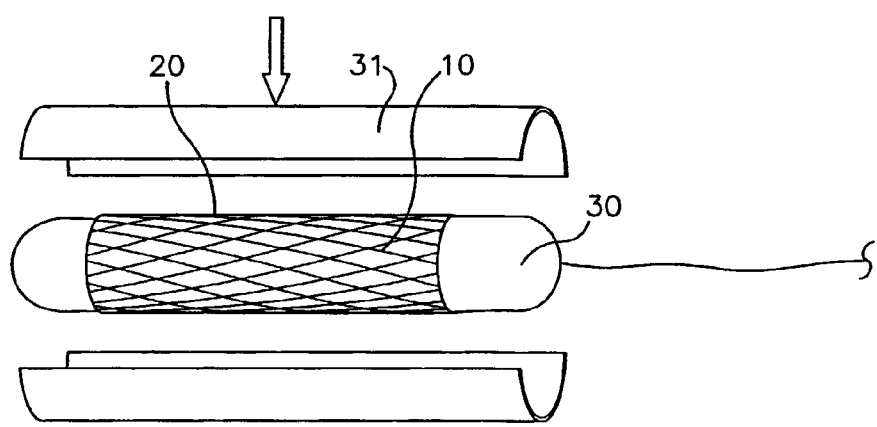
FIG. 10 schematically illustrates a partially crimped stent being crimped to an angioplasty balloon by a second crimping tool.

In the embodiments illustrated by FIGS. 8-10, the polymeric stents 10 are crimped onto angioplasty balloons 30. The stents 10 may be crimped to angioplasty balloons 30 in a variety of different ways. In the example illustrated by FIGS. 8 and 9, the stent 10 is crimped directly onto the angioplasty balloon 30. Referring to FIG. 8, the angioplasty balloon 30 is inserted into the stent 10. Referring to FIG. 9, the stent 10 is crimped to the angioplasty balloon 30 by pulling and stretching the tube.

In the example illustrated by FIG. 10, the size of the stent is initially reduced by pulling and stretching a tube 12 using an diameter setting member or contraction on a partially inflated angioplasty balloon. The angioplasty balloon 30 is then inserted into the partially crimped stent 10. The partially crimped stent 10 is crimped to the angioplasty balloon 30 using a second crimping device 31. The second crimping device 31 may be any one of the many crimping tools that are readily available.

Figure 11:
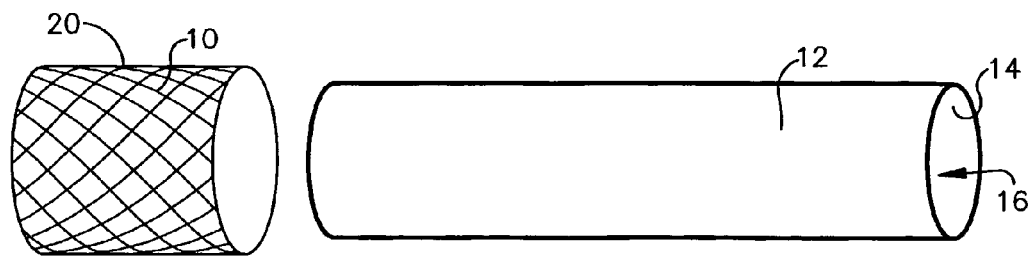
FIG. 11 is a schematic illustration of an elastic tube and a stent.
Figure 12:
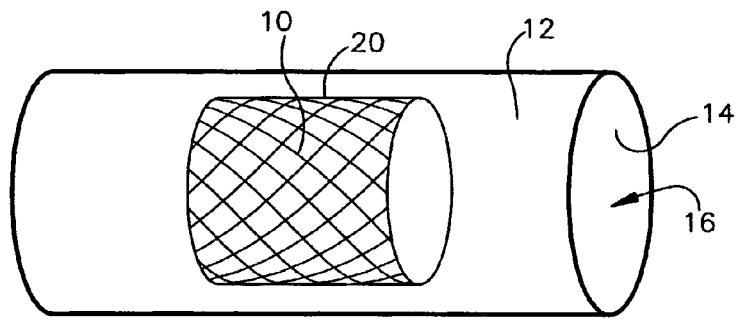
FIG. 12 is a schematic illustration showing the elastic tube of FIG. 11 swollen by solvent and disposed around the stent of FIG. 11.
Figure 13:
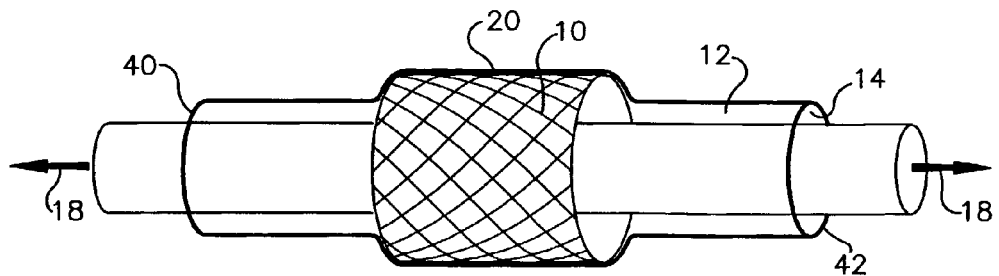
FIG. 13 is a schematic illustration of an elastic tube that conforms to an outer surface of a stent when solvent has evaporated.

FIGS. 11-13 illustrate an embodiment where the tube 12 initially has a smaller diameter than the stent 10. Referring to FIG. 12, the tube is expanded to fit over the stent 10. For example, a solvent may be added to the tube 12 to expand the tube before the stent is placed in the tube. Referring to FIG. 13, the tube 12 is then allowed to return to the tube's original size to bring the tube into contact with the stent 10. For example, a solvent in the tube may be evaporated to return the tube to its original size. The tube 12 is then pulled and stretched to crimp the stent 10.

In the example illustrated by FIGS. 11-13, the solvent is selected based on the material of the tube 12. A solvent that is compatible with the polymer chains that make up the tube material will swell the tube. The polymer chains of an elastomeric tube are cross linked and do not dissolve in the solvent. As a result, the tube retains its 3D structure and can recover its initial dimensions upon solvent evaporation or desorption. The molecules of the solvent only penetrate the polymer chains, creating space between the polymer chains without releasing (dissolving) the polymer chains. This has an effect of swelling the material. One acceptable solvent for swelling a silicone tube is cyclohexane. The silicone tube is made out of highly cross linked silicone polymers (the individual polymer chains are linked to one another). Cyclohexane can therefore penetrate between the chains and expand the space between the chains. Since the silicone chains are cross linked, individual chains are not released and the silicone material does not dissolve. The silicone tube may be dipped in cyclohexene for 30 seconds or more or for the time necessary to reach a larger diameter allowing insertion of the open stent. As the silicone absorbs the cyclohexane, the polymer swells and increases the diameter of the tube. As the cyclohexane is evaporated the silicone tube slowly recovers its original dimensions. The tube can be pulled and stretched in a variety of different ways. For example, first and second end portions 40, 42 of the tube may be pulled in opposite directions or the position of one end of the tube may be secured, while the second end of the stent is pulled.

Figure 14:
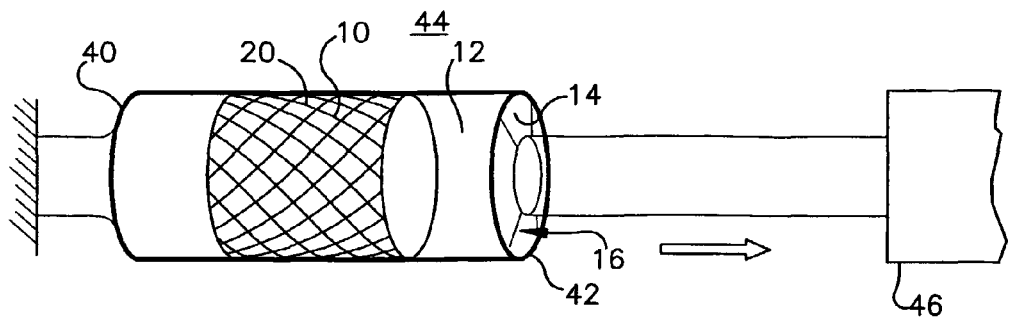
FIG. 14 schematically illustrates an apparatus for crimping a stent.
Figure 15:
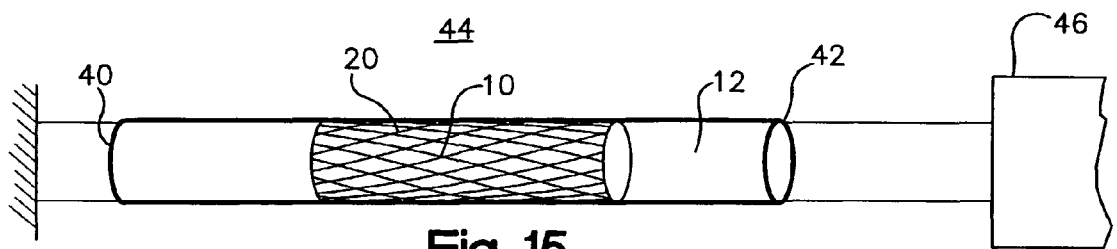
FIG. 15 schematically illustrates an apparatus for crimping a stent.

FIGS. 14 and 15 schematically illustrate an example of an apparatus 44 for crimping stents 10. The apparatus 44 includes an elastic tube 12 and an actuator 46. The actuator 46 is coupled to the elastic tube 12. In the example illustrated by FIGS. 14 and 15, the position of the first end 40 of the elastic tube is fixed and the second end 42 of the elastic tube is connected to the actuator 46. Movement of the actuator 46 increases a length of the elastic tube 12 and decreases an extent of the passage 16. The inner surface 14 of the tube engages the outer surface of the stent to crimp the stent.

Figure 16:
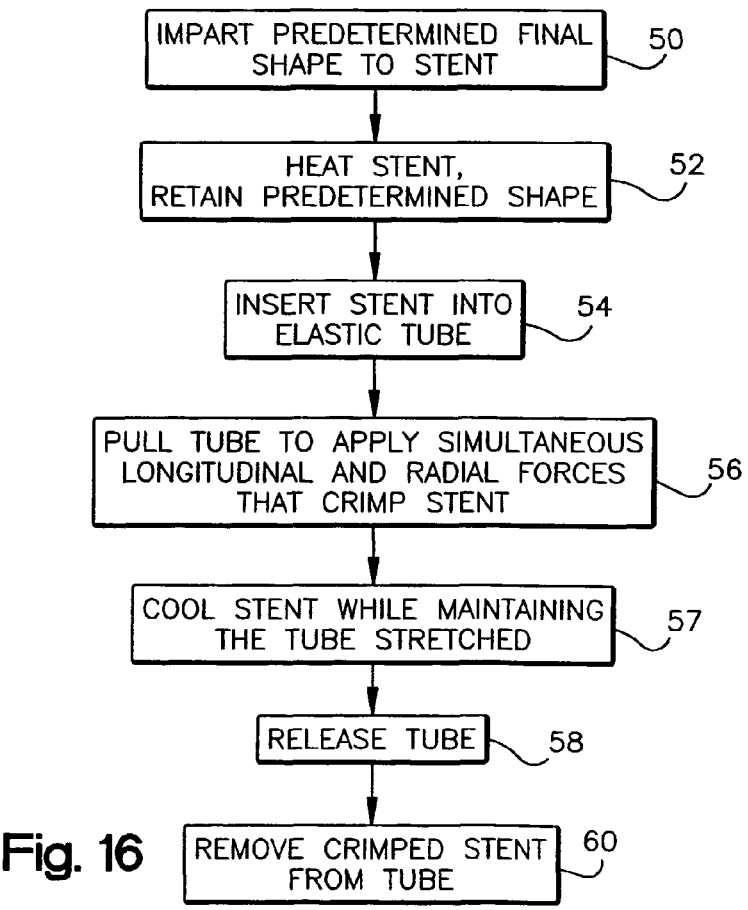
FIG. 16 is a flowchart that illustrates a method of crimping a stent.

FIG. 16 is a flow chart that illustrates an exemplary method of crimping a polymer-based stent. A desired final size and/or shape is imparted 50 to the stent before the stent is crimped. For example, the polymer may be extruded into a tube at the final desired diameter. The tube is heated and cooled to educate the tube at the desired diameter. The tube may then be cut to define the desired lattice of the stent. The selected or predetermined size and/or shape may correspond to the intended size and/or shape of the stent when deployed in the patient's vasculature. Acceptable methods of imparting a desired final size and shape to a stent are taught in PCT Application No. 04/04133, filed on Apr. 2, 2004, entitled "Polymer Based Stent Assembly," assigned to the assignee of the present application, and U.S. patent application Ser. No. 10/508,739, filed on Sep. 21, 2004, entitled "Polymer Based Stent Assembly," assigned to the assignee of the present invention. PCT Application No. 04/04133 and U.S. patent application Ser. No. 10/508,739 are incorporated herein by reference in their entirety. The stent is heated 52 such that the predetermined size and shape imparted to the stent is retained by the stent. For example, the stent may be heated to a temperature above a glass transition temperature of the stent before crimping the stent, while retaining the chain entanglement generated during the processing or the education of the desired stent size and shape. Different heat cycles are used to help either soften the polymer to allow better deformation or to stiffen the polymer for it to remain in a deformed shape. PCT Application No. 04/04133 and U.S. patent application Ser. No. 10/508,739 provide examples that illustrate how the predetermined size and shape imparted to the stent can be retained when the stent is heated to a temperature above the glass transition temperature of the stent for a period of time that does not erase the size and shape imparted before crimping. The stent is inserted 54 into the elastic tube 12 before or after the stent is heated to a rubbery state. The tube is pulled 56 to stretch the tube and apply simultaneous longitudinal and radial forces that crimp the stent. The stent 10 is allowed to cool 57 and the tube is released 58. The crimped stent, retaining the intended shape, is removed 60 from the tube.

EXAMPLE 1

Crimping on a Metal Support

A silicone tube having an inside diameter of 2.8 mm. is provided. A stent formed from a polymeric material, such as amorphous PLA75 (polymer chains composed of 75% L-/25% D-lactyl units; Mw=115 kDa) having an outside diameter of 3.6 mm is provided. The tube is soaked in a solvent to swell the tube to have an inside diameter above 3.6 mm. The stent is slipped into the tube. The solvent evaporates and the tube shrinks back to its initial diameter and tightly covers the stent. A metal support with diameter of 1.6 mm is placed inside the stent to act as a support. Before stretching the tube, the temperature of the assembly is raised to 65° C. for a period of 1 minute to put the stent in a rubbery state. The tube is then stretched by pulling both ends until the stent is snugly crimped to the support. While holding the tube stretched thus maintaining the two forces, the assembly is rapidly cooled to room temperature in order to change the polymer stent to the glassy state. After the assembly is cooled, the ends of the tube are released and the tube returns to its original size and diameter. The stent stays at the diameter of the metal support. The stent elongates from 16 to 19 mm during the crimping process. The inside diameter of the stent is reduced from 3.2 mm to 1.8 mm. The stent is then removed from the metal support and placed over an angioplasty balloon. A final crimping is performed to reduce the stent diameter from 1.8 mm to 1.3 mm with a standard crimping tool and under the heating conditions used to crimp the stent with the tube.

EXAMPLE 2

Crimping Directly on a Angioplasty Balloon

A silicone tube having an inside diameter of 2.8 mm. is provided. A stent formed from a polymeric material, such as amorphous PLA75 (polymer chains composed of 75% L-/25% D-lactyl units; Mw=115 kDa) having an outside diameter of 3.6 mm is provided. The tube is soaked in a solvent to swell the tube to have an inside diameter above 3.6 mm. The stent is slipped into the tube. The solvent evaporates and the tube shrinks back to its initial diameter and tightly covers the stent. An angioplasty balloon is then inserted inside the stent. Before stretching the tube, the temperature of the assembly is raised to 65° C. for a period of 1 minute to put the stent in a rubbery state. The tube is then stretched by pulling both ends until the stent is snugly crimped on the angioplasty balloon. While holding the tube stretched thus maintaining the two forces, the assembly is rapidly cooled to room temperature in order to change the polymer stent to the glassy state. After the assembly is cooled, the ends of the tube are released and the tube returns to its original size and diameter. The stent stays at the diameter of the angioplasty balloon. The stent elongates from 16 to 22 mm during the crimping process. The inside diameter of the stent is reduced from 3.2 mm to 1.3 mm.

While the invention has been described with reference to specific embodiments, it will be apparent to those skilled in the art that may alternatives, modifications, and variations may be made. Accordingly, the present invention is intended to embrace all such alternatives, modifications, and variations that may fall within the spirit and scope of the appended claims.

The invention claimed is:

1. A method of crimping a polymeric stent, comprising:
   a) inserting the stent into an elastic tube having an inner surface that defines a passage;
   b) pulling the tube to cause stretching of the tube, such that the inner surface of the tube engages an outer surface of the stent and applies simultaneous longitudinal and radial forces to the outer surface of the stent to thereby simultaneously reduce a radial extent of the stent and increase a longitudinal extent of the stent; and
   c) releasing the tube to allow the tube to return to an undeformed size.

2. The method of claim 1 wherein the first and second end portions are pulled in opposite directions to impart simultaneous compressing and elongating forces to the outer surface of the stent.

3. The method of claim 1 further comprising removing a crimped stent from the tube.

4. The method of claim 1 wherein the tube is an elastic silicone tube.

5. The method of claim 1 further comprising imparting a predetermined final size and shape to the stent before crimping the stent.

6. The method of claim 5 further comprising cooling the stent, releasing the tube to allow the tube to return to its original shape, and removing the crimped stent from the tube.

7. The method of claim 1 further comprising heating the stent around the glass transition temperature of the stent before crimping the stent.

8. The method of claim 1 wherein the elastic tube is made from an elastomeric polymer and wherein a diameter of the tube is reduced upon stretching of the tube.

9. The method of claim 1 further comprising inserting a diameter setting member into the stent before crimping the stent to define a diameter of the crimped stent.

10. The method of claim 1 wherein an inner surface of the tube adheres to an outer surface of the stent to apply simultaneous longitudinal and radial forces to the stent.

11. The method of claim 1 wherein the stent is crimped to an angioplasty balloon by pulling the tube.

12. The method of claim 1 further comprising removing the stent from the tube and crimping the stent to an angioplasty balloon with a second crimping device.

13. The method of claim 1 wherein a solvent is added to the tube to expand the tube before the stent is placed in the tube and evaporating the solvent to bring the tube into contact with the stent.

14. An apparatus for crimping a polymeric stent having an outer surface, comprising:
   a) an elastic tube having an inner surface that defines a passage that is sized to fit over the outer surface of the stent;
   b) an actuator coupled to the elastic tube, wherein movement of the actuator increases a length of the elastic tube and decreases an extent of the passage, wherein the inner surface of the tube engages the outer surface of the stent and reduces an extent of the stent to thereby crimp the stent; and
   c) a heating element for heating the stent around the glass transition temperature of the stent before crimping the stent.

15. The apparatus of claim 14 wherein the increase in length of the elastic tube and the decrease in extent of the passage of the tube reduces a diametric extent of the stent and increases a longitudinal extent of the stent.

16. The apparatus of claim 14 wherein the actuator pulls first and second end portions of the elastic tube in opposite directions to impart simultaneous compressing and elongating forces to the outer surface of the stent.

17. The apparatus of claim 14 wherein the tube is an elastic silicone tube.

18. The apparatus of claim 14 further comprising a diameter setting member that is inserted into the stent before crimping the stent to define a diameter of the crimped stent.

19. A method of preparing a polymeric stent for application in vasculature of a patient, comprising:

a) imparting predetermined final size and shape to the stent by heating the stent to a temperature above the glass transition temperature of the stent such that the predetermined size and shape is retained and then cooling the stent;
b) inserting the stent into an elastic tube having an inner surface that defines a passage;
c) heating the stent to a temperature at or above a glass transition temperature such that the imparted final size and shape is retained by the stent;
d) pulling the tube to cause stretching of the tube, such that the inner surface of the tube engages an outer surface of the stent and applies simultaneous longitudinal and radial forces to the outer surface of the stent to thereby simultaneously reduce a radial extent of the stent and increase a longitudinal extent of the stent;
e) cooling the stent to a temperature below the glass transition temperature;
f) releasing the tube, such that at least a portion of the inner surface of the tube disengages at least a portion of the outer surface of the stent; and
g) removing the stent from the tube.

* * * * *